United States Patent [19]
Fox et al.

[11] Patent Number: 5,876,328
[45] Date of Patent: Mar. 2, 1999

[54] SURGICAL CAMERA DRAPE ASSEMBLY AND METHOD

[75] Inventors: Richard Q. Fox; David P. Chapman, both of Orlando, Fla.

[73] Assignee: Endolap, Inc., Orlando, Fla.

[21] Appl. No.: 839,202

[22] Filed: Apr. 23, 1997

[51] Int. Cl.⁶ ........................................................ A61B 1/04
[52] U.S. Cl. ............................................ 600/122; 600/121
[58] Field of Search .................................... 600/121, 122, 600/112; 128/917, 918, 919, 844, 849, 853, 856; 359/510; 354/62

[56] References Cited

U.S. PATENT DOCUMENTS

| | | |
|---|---|---|
| Re. 34,002 | 7/1992 | Adair . |
| 4,522,196 | 6/1985 | Cunningham et al. . |
| 4,522,305 | 6/1985 | Jacobsson . |
| 4,757,381 | 7/1988 | Cooper et al. . |
| 5,078,483 | 1/1992 | Herzberg . |
| 5,168,863 | 12/1992 | Kurtzer . |
| 5,239,981 | 8/1993 | Anapliotis . |
| 5,274,500 | 12/1993 | Dunn . |
| 5,301,657 | 4/1994 | Lafferty et al. . |
| 5,311,358 | 5/1994 | Pederson et al. . |
| 5,325,846 | 7/1994 | Szabo . |
| 5,406,939 | 4/1995 | Bala . |
| 5,425,583 | 6/1995 | Wild . |
| 5,429,118 | 7/1995 | Cole et al. . |
| 5,433,221 | 7/1995 | Adair . |
| 5,467,223 | 11/1995 | Cleveland, Jr. et al. . |
| 5,496,259 | 3/1996 | Perkins . |
| 5,498,230 | 3/1996 | Adair . |

Primary Examiner—Beverly M. Flanagan
Attorney, Agent, or Firm—Allen, Dyer, Doppelt, Milbrath & Gilchrist, P.A.

[57] ABSTRACT

A surgical drape having a transparent, flexible tubular body for enclosing a non-sterile video camera includes a closed end and an opening adjacent the closed end. A flat reinforcing washer formed to the tubular body adjacent the opening defining an access opening into the tubular body for receiving a male threaded connection of a sterile camera coupler. The access opening of the reinforcing washer is sized to snugly fit the male threaded connection of the coupler so that the drape is readily secured to the coupler for providing an effective seal. When the coupler is screwed onto the camera, there is a clear optical channel between the camera and the coupler. With such an arrangement, the coupler is accessible from outside the drape. The drape separates the camera from the coupler and in operation, the coupler is sterilized prior to the start of the surgical procedure. As a result, both the coupler and the endoscope are easily accessible during the procedure.

42 Claims, 4 Drawing Sheets

SURGICAL CAMERA DRAPE ASSEMBLY AND METHOD

FIELD OF INVENTION

The invention relates generally to medical devices, and more particularly to a sterile drape for an endoscope camera.

BACKGROUND OF THE INVENTION

For a typical camera and endoscope assembly as used in minimally invasive surgery (MIS), the camera is connected to a coupler, which, in turn, is connected to the eyepiece of a rigid endoscope. The use of drapes provides a solution to the well-known problem of sterility in the operating room. When drapes are used, the camera and coupler are non-sterile, while the endoscope is sterile. A tubular plastic drape is positioned around the camera and coupler in order that they may be used within the sterile field around the operating table. Frequently, they are laying on the patient.

Using a conventional drape, at the start of the MIS procedure, a nurse pushes the eyepiece of the endoscope through a small elastic hole in the camera drape, and attaches the endoscope to the coupler and camera. Once this step is performed, the MIS procedure may continue. However, the eyepiece of the scope is now considered non-sterile, and may not be removed from the drape during the remainder of the procedure. If the physician wishes to change the endoscope or refocus the camera coupler during the procedure, the nurse must typically struggle with the manipulation of complex mechanical and optical parts located within the plastic drape.

Another conventional approach is to put a transparent optical grade window in the drape, so that the camera remains inside the drape, and the endoscope remains outside the drape. In most instances, the window is of necessity a lens because its existence changes the focal length of the optical train. Such a lens is expensive, but the lack of a lens often provides unwanted magnification at the camera and unwanted reduction in field of view. Further, camera drapes are typically single use items. Once they are used, they are no longer sterile. The cost of a high quality optical window in a drape that will see use only once is simply too high.

U.S. Pat. No. 5,433,221 to Adair discloses a windowed drape for a surgical camera which includes a cylindrical generally flexible non-elastic body and a flexible elastic end portion having an optically clear window integrally formed with the distal end portion. The surgical camera and coupler are positioned within the drape. The coupler and endoscope connection is made with the window therebetween. As disclosed in the patent, a well known shortcoming in the art includes the lack of high quality optically clear material for the windows.

SUMMARY OF INVENTION

In the present invention, the drape separates the camera from the coupler. The non-sterile camera is covered by the drape as before. However, the coupler is now sterilized prior to the start of the MIS procedure, and both the coupler and the endoscope are easily accessible during the procedure. If the physician wishes to change the endoscope during the procedure, the nurse has full access to the components which must be manipulated.

A properly sized re-enforcing member or washer is connected to the tubular body of the drape adjacent an end thereof. The inner diameter of the washer is sized to fit snugly around the threads of the coupler. In addition, the thickness of the washer is about the thickness of the thread spacing to provide a more effective seal. The coupler may be threaded into the washer, and the camera and its cable are advanced into the tubular body of the drape. The coupler may then be rotated to secure the coupler and camera together. The optical focusing ring of the coupler is outside of the drape for easier manipulation.

When the coupler is screwed onto the camera, there is a clear optical channel between the camera and the coupler. No optical window is used. Sterility is still maintained and replacement of the endoscope or adjustment to the coupler is easy to perform. The cost of the disposable drape according to the invention is also relatively low when compared to that found in the art.

Another feature of the drape is its folded shipping state wherein telescoping folds are formed in the tubular body portion. In this state, no potential pockets are presented to the camera as it is advanced through the drape.

A method aspect of the invention includes providing a drape for covering the non-sterile camera. The drape comprises the tubular body for enclosing the camera therein and the opening adjacent the distal end for receiving the coupler. The drape further comprises the reinforcing washer connected to the tubular body adjacent the opening. The reinforcing washer defines an access opening into the tubular body for receiving a male connecting portion of the coupler. The access opening of the reinforcing washer is sized to snugly fit upon the male connecting portion of the coupler for readily securing the camera drape to the coupler and so that the coupler is accessible from outside the drape. The camera is positioned within the drape tubular body. The male connecting portion of the coupler extends outwardly from a first end of the body portion for mating with the camera. A second connecting portion at a second connecting portion at a second end of the coupler body portion is used for connecting the coupler to the endoscope. The coupler male connecting portion is passed through the access opening defined by the washer and secured to the camera wherein the washer snugly fits the coupler. In a preferred method of use for the present invention, the coupler is secured to the washer, and then the coupler is secured to the camera while secured to the washer. A sterile endoscope is then secured to the coupler second connecting portion.

BRIEF DESCRIPTION OF DRAWINGS

A preferred embodiment of the invention as well as alternate embodiments are described by way of example with reference to the accompanying drawings in which.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
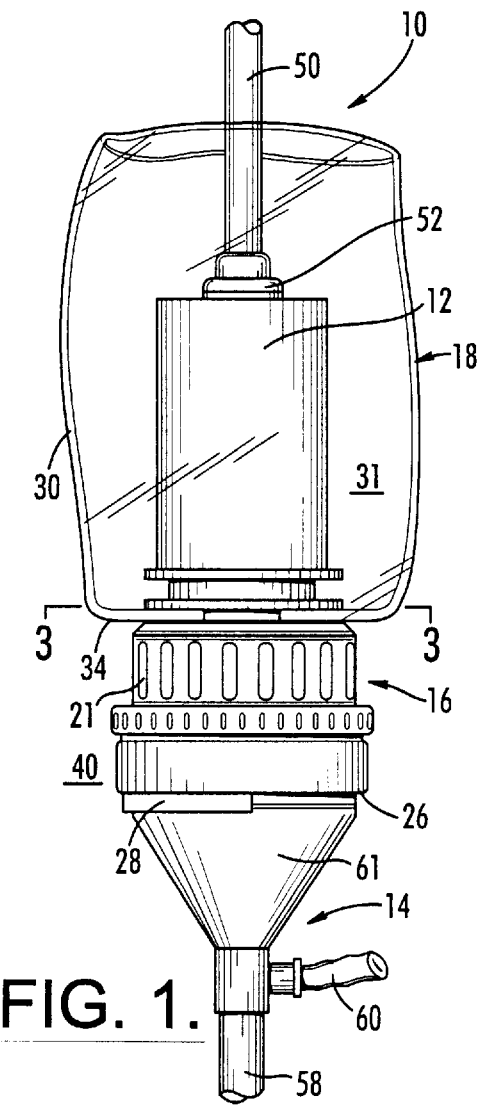
FIG. 1 is a side elevational view of a surgical camera and endoscope assembly of the present invention.

Referring now to FIG. 1, a surgical camera and endoscope assembly 10 comprises a non-sterile camera 12 for use with a sterile endoscope 14, a sterile coupler 16, coupling the camera 12 to the endoscope 14, and a drape 18 for covering the non-sterile camera.

Figure 2:
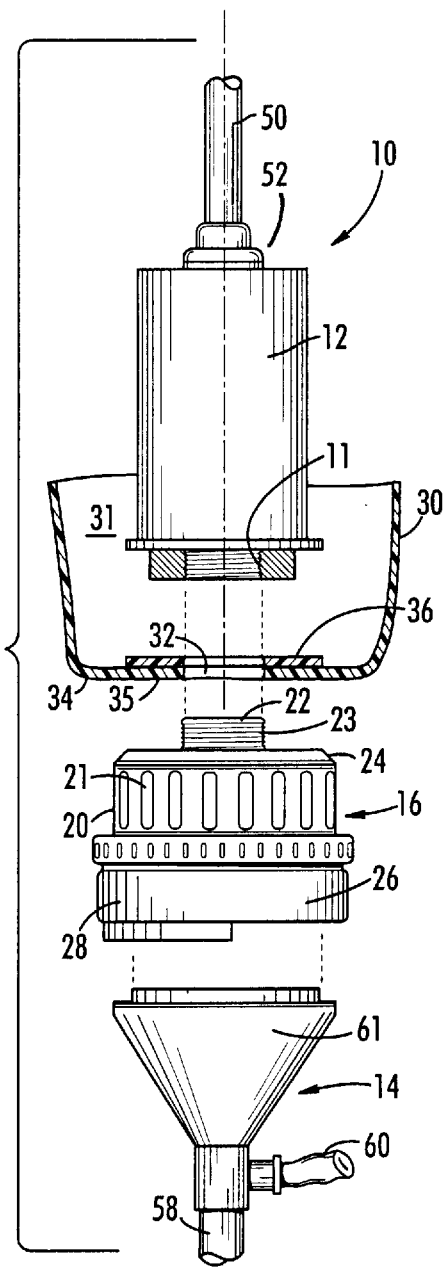
FIG. 2 is an exploded view of the surgical camera and endoscope assembly of FIG. 1.

As illustrated with reference to FIG. 2, the coupler 16 comprises a body portion 20, a male connecting portion or connection 22 extending outwardly from a first end 24 of the body portion 20 for mating a female connecting portion 11 of with the camera 12. The coupler 16 further includes a second connecting portion 26 at a second end 28 of the body portion 20 for connecting to the endoscope 14. A preferred embodiment of the drape 18 of the present invention comprises a flexible, transparent tubular body 30 enclosing the camera 12 and an opening 32 within a sidewall 35, adjacent a closed drape distal end 34. In addition, a generally flat, reinforcing washer 36 is connected to the tubular body 30 adjacent the opening 32.

As illustrated, again with reference to FIGS. 1 and 2, one preferred embodiment of the present invention places the washer 36 inside 31 the tubular body 30. Such an arrangement provides strength to overcome forces pulling against the washer 36 when the coupler pulls against the washer as the camera 12 is inserted within the tubular body 30, or when the coupler 16 pulls against the washer 36 under the influence of gravity.

Figure 3A:
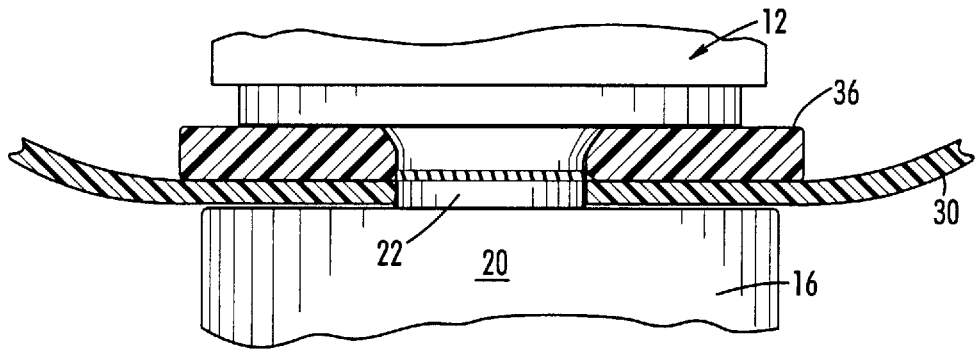
FIG. 3a is a greatly enlarged cross-sectional view taken along lines 3—3 of FIG. 1.
Figure 3B:
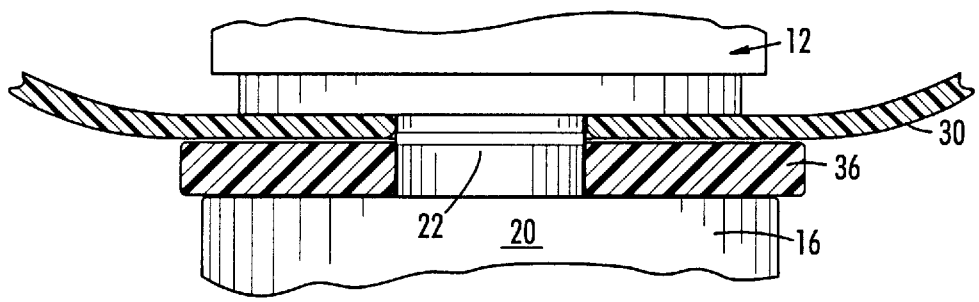
FIGS. 3b and 3c are cross-sectional views illustrating alternate embodiments of a reinforcing washer and tubular body useful in the present invention.
Figure 3C:
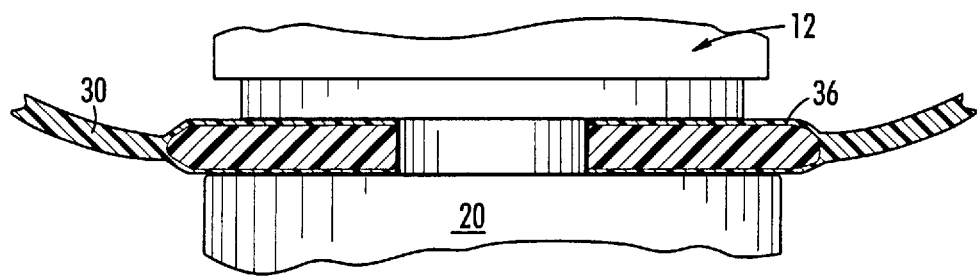

It is not uncommon for the coupler 16 to pull against the washer 36 when the camera 12 is being fished down the folded drape. Typically, during this procedure, then coupler 16 is secured to the washer 36, but is dangling at the bottom of the drape 18. In a preferred embodiment of the present invention, the washer 36 is made from a plastic material stiffer than the flexible drape body 30, yet flexible. The reinforcing washer 36 defines an access opening 38 into the tubular body 30 through which the first male connecting portion 22 of the coupler 16 passes. The access opening 38 of the reinforcing washer 36 is sized to snugly fit upon the first male connecting portion 22 of the coupler 16, as further illustrated with reference to FIG. 3, so that the camera drape 18 is readily secured to the coupler 16 and so that the coupler 16, and in particular, a focus ring 21, by way of example, is accessible from outside 40 the drape 18. Alternate embodiments include the washer 36 attached to the outside of the tubular body 30 and integrally formed within a wall of the body as illustrated with reference to FIGS. 3b and 3c. As illustrated again with reference to FIGS. 2 and 3, the coupler first male connecting portion 22 comprises outside threads 23 adapted for threaded attachment to the camera 12 wherein the washer 36 has a thickness dimension for compatibly engaging the coupler threaded male connecting portion 22 thus fitting between the threads 23.

The present invention thus provides for securing the coupler 16 to the washer 36 and thus the drape 18. A seal is sized for the snug fit to the male connection 22. As a result, a sterile field is maintained.

Figure 4:
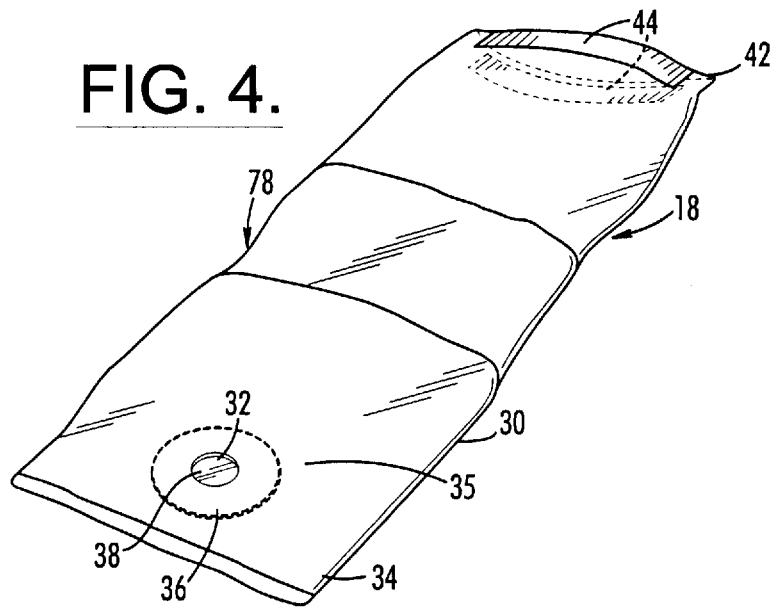
FIG. 4 is a perspective view of the drape of the present invention in a partially extended arrangement.

As illustrated again with reference to FIG. 1, the drape 18 comprises a tubular body 30 having a diameter sized for receiving the camera 12. As illustrated with reference to FIG. 4, the drape 18 includes an open proximal end 42 sized for receiving the camera 12 therethrough. Both the diameter and the proximal opening may be approximately five to ten inches.

Further, the drape 18, in one preferred embodiment herein described again with reference to FIG. 4, includes a closed distal end 34 and a sidewall 35, wherein the access opening 38 is through the sidewall adjacent the closed distal end.

Figure 5:
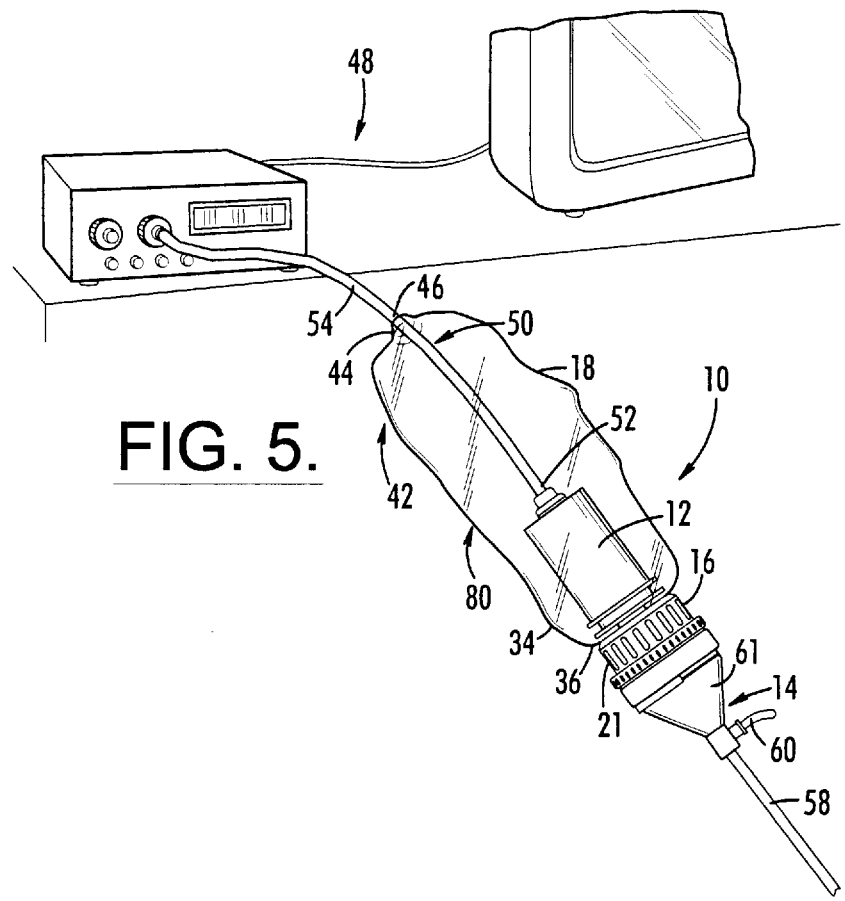
FIG. 5 is a perspective view of the drape of the present invention in use with a surgical camera and associated video equipment.

An adhesive strip 44 is attached at the drape open proximal end 42 for attaching the proximal end to a cable portion 46 of a camera cable 50 away from the camera 12, as illustrated with reference to FIG. 5. The assembly 10, as illustrated with reference again to FIG. 5, in operation typically includes a camera cable distal end 52 attachable to the camera 12 and an opposite proximal portion 54 extending through the tubular body 30 and out for connection to video operating equipment 48, such as a camera controller and monitor typically located several feet from the camera.

By way of further example, again with reference to FIG. 1, the coupler 16 includes an adjusting ring or knob 21, such as for focus adjustment, that is accessible from outside 40 the drape 18. The endoscope 14 comprises a rigid insertion tube 58, typically fiber optics cable 60 and eyepiece 61 connected to the tube 58. The eyepiece 61 is adapted for connection to the coupler second connecting portion 26, as illustrated again with reference to FIG. 2, by way of example. Various endoscopes will comprise varying connectors. Typically, eyepieces are suitable for direct visual use, and the couplers must be configured to operate suitably with the eyepiece.

Figure 6:
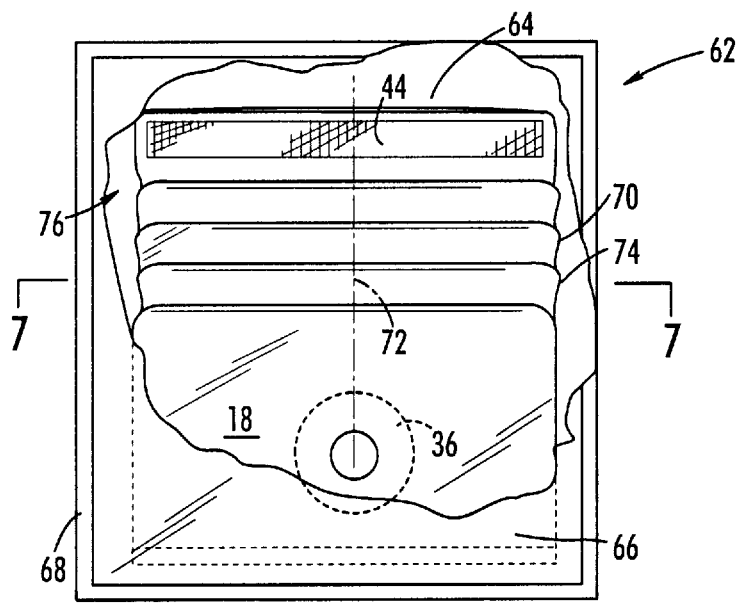
FIG. 6 is a fragmentary plan view of one embodiment of the present invention in a folded and stored position within a sterile package.
Figure 7:
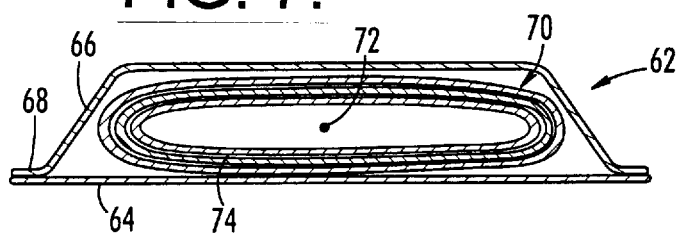
FIG. 7 is a cross-sectional view taken along lines 7—7 of FIG. 6.

In a stored arrangement of the drape 18, and as illustrated with reference to FIGS. 6 and 7, the drape 18 is carried within a package 62 having a card styled paper the couplers must be configured to operate suitably with the eyepiece.

In a stored arrangement of the drape 18, and as illustrated with reference to FIGS. 6 and 7, the drape 18 is carried within a package 62 having a card styled paper base 64 and a transparent cover 66 sealed about a peripheral portion 68 for storing the drape 18 in a sterile environment. The sterile drape 18, in its stored arrangement, includes a plurality of wall sections 70 folded onto each other along a longitudinal tubular axis 72 for forming folded layers 74 extending transversely of the direction of the tubular axis.

In one preferred method of use for maintaining a sterile field using a non-sterile surgical camera, the method comprises the steps of providing the non-sterile camera 12, providing the sterile drape 18 for covering the non-sterile camera, and positioning the camera within the drape tubular body 30 as illustrated again with reference to FIGS. 1 and 2. As illustrated again with reference to FIG. 6, the drape 18 is stored in the package 62 prior to use. When needed, the sterile drape 18 is removed from the package 62 in a sterile environment.

Prior to insertion of the camera 12 into the drape 18, the sterile coupler 16, including the coupler male connecting portion 22, is passed through the access opening 38 defined by the washer 36 for providing a seal between the coupler and the drape 18. As desired, the camera 12 is inserted into the drape 18 while the drape 18 is in a folded arrangement 76 as illustrated again with reference to FIG. 6, or in a partially extended position 78 as illustrated again with reference to FIG. 4. The coupler male connecting portion 22 is secured to the camera 12 wherein the washer 36 fits between the camera and the coupler 16. The sterile endoscope 14 is then secured to the coupler connecting portion 26. The cable 50 as earlier described, is connected for operation of the camera 12, and the drape 18 is pulled to an extended position 80 and connected at its proximal end 42 to the cable portion 46 using the adhesive strip 44 as earlier described with reference to FIG. 5.

Thus, as herein described, preferred steps in using the present invention include first connecting the sterile coupler 16 to the drape 18 while the drape is in its folded state. The combination of the drape 18 and the coupler 16 is now sterile, and the drape is now sealed to the coupler through the washer 36 as earlier described. This sealing is accomplished without glass windows, lenses, or other optical and mechanical assemblies. The second step includes positioning the camera 12 into the folded drape and securing the camera to the coupler, typically the camera having a female threaded connector and the coupler having a male threaded connector, as herein described. The third step then includes unfolding the folded drape and securing it to the camera cable 50.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and alternate embodiments are intended to be included within the scope of the appended claims.

That which is claimed is:

1. A camera and endoscope assembly comprising:
    a non-sterile camera;
    a sterile endoscope;
    a sterile coupler comprising;
        a body portion;
        a male connecting portion extending outwardly from a first end of the body portion for mating with the non-sterile camera; and
        a second connecting portion at a second end of the body portion for connecting to the endoscope; and
    a sterile drape for covering the non-sterile camera, the sterile drape comprising:
        a tubular body enclosing the non-sterile camera and having an opening adjacent a distal end thereof; and
        a reinforcing washer formed from a material stiffer than material forming the tubular body so as to provide strength, wherein the reinforcing washer is connected to the tubular body adjacent the opening, the reinforcing washer defining an access opening into the tubular body through which the male connecting portion of the coupler passes, the access opening of the reinforcing washer being sized to snugly fit upon the male connecting portion of the coupler so that the drape is sealably secured to the coupler and so that the coupler is accessible from outside the drape.

2. The assembly according to claim 1, wherein the tubular body comprises a flexible plastic material.

3. The assembly according to claim 1, wherein the tubular body is transparent.

4. The assembly according to claim 1, wherein the drape further comprises an adhesive layer adjacent a proximal end thereof.

5. The assembly according to claim 1, wherein the tubular body includes a closed distal end portion and a sidewall portion, and wherein the access opening is through the sidewall portion adjacent the closed distal end portion.

6. The assembly according to claim 1, further comprising a camera cable having a cable portion enclosed within the drape, the camera cable having a distal end portion attached to the camera and a proximal end portion for connection to video equipment.

7. The assembly according to claim 1, wherein the tubular body defines an inside surface, and wherein the reinforcing washer is connected to the inside surface.

8. The assembly according to claim 1, wherein the washer is adhesively secured to the tubular body.

9. The assembly according to claim 1, wherein the washer is generally flat.

10. The assembly according to claim 1, wherein the washer is integrally formed with the tubular body.

11. The assembly according to claim 1, wherein the coupler includes an adjusting portion accessible from outside the drape.

12. The assembly according to claim 1, wherein the male connecting portion of the coupler comprises outside threads, and wherein the washer has a thickness for compatibly engaging the outside threads.

13. A camera drape for a camera and endoscope assembly comprising a non-sterile camera and sterile coupler having a male connecting portion extending outwardly therefrom for connection to the camera, the camera drape comprising:
    a tubular body for enclosing the non-sterile camera, the tubular body having a closed distal end and an opening adjacent the distal end; and
    a reinforcing washer formed from a material stiffer than material forming the tubular body so as to provide strength, wherein the reinforcing washer is connected to the tubular body adjacent the opening, the reinforcing washer defining an access opening into the tubular body for receiving the male connecting portion of a coupler, the access opening of the reinforcing washer being sized to snugly fit upon the male connecting portion of the coupler so that the drape is sealably secured to the coupler and so that the coupler is accessible from outside the drape.

14. The drape according to claim 13, wherein the tubular body comprises a flexible plastic material.

15. The drape according to claim 13, wherein the tubular body is transparent.

16. The drape according to claim 13, further comprising an adhesive layer adjacent a proximal end thereof.

17. The drape according to claim 13, wherein the tubular body includes a closed distal end portion and a sidewall portion, and wherein the access opening is through the sidewall portion adjacent the closed distal end portion.

18. The drape according to claim 13, wherein the tubular body defines an inside surface, and wherein the reinforcing washer is connected to the inside surface.

19. The drape according to claim 13, wherein the washer is generally flat.

20. The drape according to claim 13, wherein the washer is adhesively secured to the tubular body.

21. The drape according to claim 13, wherein the male connecting portion of the coupler comprises outside threads, and wherein the washer has a thickness for compatibly engaging the outside threads.

22. An drape according to claim 13, wherein the drape, when in a stored position has a plurality of sections folded onto each other along a longitudinal axis.

23. A camera drape for a camera and endoscope assembly comprising a non-sterile camera and sterile coupler having a male connecting portion extending outwardly therefrom for connection to the camera, the camera drape comprising:

a package for carrying a sterile drape therein; and a sterile drape carried within the package, the sterile drape comprising:

a tubular body having a distal end and an opening adjacent the distal end, the tubular body further having an open proximal end for receiving a camera therethrough; and a reinforcing washer formed from a material stiffer than material forming the tubular body so as to provide strength, wherein the reinforcing washer is connected to the tubular body adjacent the opening, the reinforcing washer defining an access opening into the tubular body for receiving the male connecting portion of the coupler, the access opening of the reinforcing washer being sized to snugly fit upon the male connecting portion of the coupler so that the drape is readily secured between the coupler and the camera, the coupler being accessible from outside the drape.

24. The drape according to claim 23, wherein the tubular body comprises a transparent material.

25. The drape according to claim 23, wherein the washer is flat.

26. The drape according to claim 23, wherein the package comprises a transparent wall for viewing the drape through the wall.

27. The drape according to claim 23, further comprising an adhesive layer adjacent a proximal end thereof.

28. The assembly according to claim 23, wherein the tubular body defines an inside surface, and wherein the reinforcing washer is connected to the inside surface.

29. The drape according to claim 23, wherein the drape has a plurality of sections folded onto each other along a longitudinal axis.

30. A method for maintaining a sterile field using a non-sterile camera and a sterile coupler, the method comprising the steps of:

providing a drape for covering the non-sterile camera, the drape comprising a tubular body for enclosing the camera therein and an opening adjacent a distal end thereof, the drape further comprising a reinforcing washer formed from a material stiffer than material forming the tubular body so as to provide strength, wherein the reinforcing washer is connected to the tubular body adjacent the opening, the reinforcing washer defining an access opening into the tubular body for receiving a male connecting portion of a coupler therethrough, the access opening of the reinforcing washer being sized to snugly fit upon the male connecting portion of the coupler for securing the camera drape to the coupler and so that the coupler is accessible from outside the drape;

passing the coupler male connecting portion through the access opening defined by the washer, the washer snugly fitting the male connecting portion for sealably connecting the drape to the coupler;

positioning the camera within the tubular body of the drape; and securing the coupler male connecting portion to the camera thus providing a sterile band to the camera.

31. The method according to claim 30, further comprising the steps of:

providing a sterile endoscope; and securing the endoscope to the coupler.

32. The method according to claim 30, wherein the tubular body comprises a transparent flexible plastic material.

33. The method according to claim 30, wherein the camera positioning step comprises the step of passing the camera through a drape open proximal end sized for receiving the camera therethrough.

34. The method according to claim 30 further comprising the steps of placing an adhesive layer proximate the proximal end opening and attaching the drape proximal end to an object.

35. The method according to claim 30, further comprising the steps of connecting a camera cable to the camera and enclosing a portion of the camera cable within the drape.

36. The method according to claim 30, wherein the tubular body defines an inside surface and wherein the reinforcing washer is connected to the inside surface.

37. The method according to claim 30, wherein the reinforcing washer is integrally formed with the tubular body.

38. The method according to claim 30, further including the step of adjusting the coupling from outside the drape.

39. The method according to claim 30, wherein the coupler male connecting portion comprises outside threads for attaching the coupler to the camera and the washer has a thickness for sealably engaging the outside threads.

40. The method according to claim 30, wherein the drape providing step further includes the steps of:

folding sections of the tubular body onto each other along a longitudinal axis for forming folded layers;

providing a sterile package; and storing the folded drape in the sterile package.

41. A camera drape for a camera and endoscope assembly, which assembly includes a non-sterile camera and sterile coupler having a male connecting portion extending outwardly therefrom for connection to the camera, the camera drape comprising:

a tubular body for enclosing a non-sterile camera, the tubular body having a closed distal end and an opening within a sidewall portion adjacent the closed distal end; and a reinforcing washer connected to the tubular body adjacent the opening, the reinforcing washer defining an access opening into the tubular body for receiving a male connecting portion of a coupler, the access opening of the reinforcing washer being sized to snugly fit upon the male connecting portion of the coupler for sealably securing the drape to the coupler and for providing access to the coupler from outside the drape.

42. A camera drape for a camera and endoscope assembly, which assembly comprises a non-sterile camera and sterile coupler including a male connecting portion having outside threads, which male connecting portion extends outwardly therefrom for connection to the camera, the camera drape comprising:

a tubular body for enclosing a non-sterile camera, the tubular body having a closed distal end and an opening adjacent the closed distal end; and a reinforcing washer connected to the tubular body adjacent the opening, the reinforcing washer defining an access opening into the tubular body for receiving a male connecting portion of a coupler, the access opening of the reinforcing washer being sized to snugly fit upon the male connecting portion of the coupler, and wherein the thickness of the washer compatibly engages outside threads of the coupler sealably securing the drape to the coupler and for providing access to the coupler from outside the drape.

* * * * *